United States Patent [19]

Redmore

[11] 4,048,264
[45] Sept. 13, 1977

[54] POLYMERIC PHOSPHORAMIDES

[75] Inventor: Derek Redmore, Ballwin, Mo.

[73] Assignee: Petrolite Corporation, St. Louis, Mo.

[21] Appl. No.: 619,516

[22] Filed: Oct. 3, 1975

Related U.S. Application Data

[60] Continuation of Ser. No. 26,402, April 7, 1970, abandoned, which is a division of Ser. No. 596,798, Nov. 25, 1966, Pat. No. 3,524,908.

[51] Int. Cl.² .............................................. C07F 9/24
[52] U.S. Cl. .................................. 260/929; 260/926; 260/927 R; 260/928; 260/958
[58] Field of Search .................... 260/929, 970, 928

[56] References Cited
U.S. PATENT DOCUMENTS 3,932,565   1/1976   Batorewicz ................ 260/929 X Primary Examiner—Anton H. Sutto
Attorney, Agent, or Firm—Sidney B. Ring; Hyman F. Glass

[57] ABSTRACT

Polymeric phosphoramides — these are illustrated by polymeric phosphoramides of the formula unit

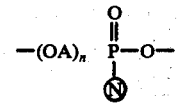

where OA is an oxirane derived unit, $n$ is a number and $N$ is an amine moiety; and to uses thereof.

6 Claims, No Drawings

POLYMERIC PHOSPHORAMIDES

The application is a continuation of Ser. No. 26,402 filed Apr. 7, 1970, now abandoned, which is a division of Ser. No. 596,798 filed Nov. 25, 1966, now U.S. Pat. No. 3,524,908, issued Aug. 18, 1970.

This invention relates to phosphoramides. More particularly, this invention relates to phosphoramideesters containing at least one

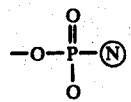

unit.

This invention also relates to uses for phosphoramides, including their use as corrosion inhibitors.

These compounds are characterized by at least one

unit, and in the preferred embodiment by at least one

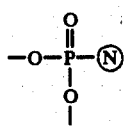

unit, where Ⓝ is an amino-derived moiety.

They may be illustrated by the following non-limiting examples where A is alkylene and R is the alcohol moiety and R' is an amino substitution and is hydrocarbon, alkyl, etc.

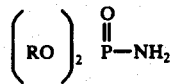

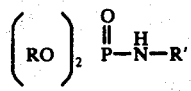

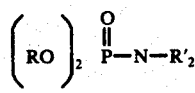

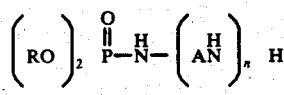

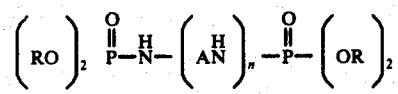

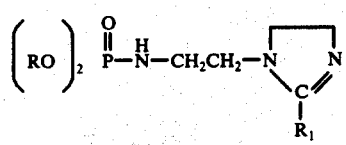

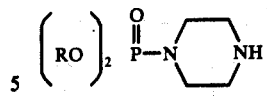

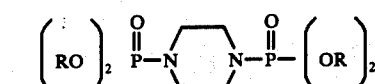

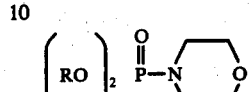

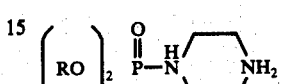

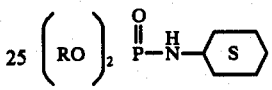

They also include polymers, for example

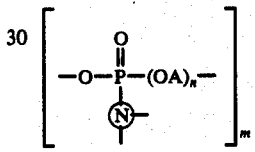

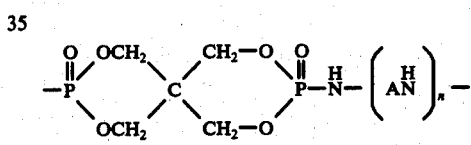

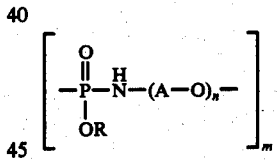

The phoophorus compound which is reacted with the amine to form the amide is a derivative of phosphorous acid,

such as esters thereof

including polymeric esters such as

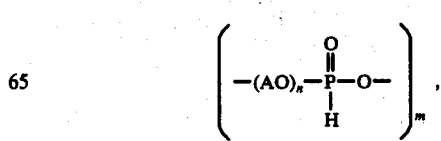

etc., which contain at least one

unit or its equivalent which unit is capable of reacting with an amine to form an amide

Stated another way, the phosphorus-containing unit as a monomer or polymer is derived from phosphorous acid, a derivative, or an equivalent thereof.

A wide variety of mono- and poly- amines having at least one primary or secondary amino group can be employed. They include aliphatic, cycloaliphatic, aryl, heterocyclic, etc. amines. These amines may or may not contain other groups. The following are representative examples.

| | |
|---|---|
| n-Butyl amine | Furfurylamine |
| Dibutyl amine | Dodecylamine |
| 2-ethylhexyl amine | Monoethanolamine |
| Di(2-ethylhexyl) amine | Diethanolamine |
| Monoisopropanolamine | N-methyl ethanolamine |
| Diisopropanolamine | N-ethy ethanolamine |
| Methyl isopropanolamine | n-Amylamine |
| Butyl isopropanolamine | Di-n-amylamine |
| Hexylamine | Sec-amylamine |
| Dihexylamine | N-ethylbutylamine |
| Heptylamine | 2-amino-4-methylpentane |
| Octylamine | 4-amino-2-butanol |
| Dioctylamine | 5-isopropylamino-1-pentanol |
| Decylamine | |

Similarly, secondary high molecular weight aliphatic amines known as Armeen 2C and Armeen 2HY can be used. (RR'NH)

Also, high molecular weight aliphatic amines known as Armeen 10, Armeen 16D, Armeen HTD, Armeen 18D, and Armeen CD can be used. ($RNH_2$)

Suitable amines having an aromatic ring include alphamethylbenzylamine and alpha-methylbenzylmonoethanolamine.

Other amines include:
2-amino-2-methyl-1-propanol
2-amino-2-methyl-1,3-propanediol
2-amino-2-ethyl-1,3-propanediol
3-amino-2-methyl-1-propanol
2-amino-1-butanol
3-amino-2,2-dimethyl-1-propanol
2-amino-2,3-dimethyl-1-propanol
2,2-diethyl-2-amino ethanol
2,2-dimethyl-2-amino ethanol
3-amino-1,2-butanediol
4-amino-1,2-butanediol
2-amino-1,3-butanediol
4-amino-1,3-butanediol
2-amino-1,4-butanediol
3-amino-1,4-butanediol
1-amino-2,3-butanediol Amines having ring structures include cyclohexylamine, dicyclohexylamine, and various comparable amines with alkyl substituents in the ring.

A wide variety of polyamines having at least one amidifiable amino group can be employed. These include the polyalkylene polyamines such as of the formula:

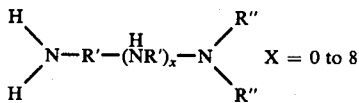

in which R" is hydrogen, alkyl, cycloalkyl, aryl, or aralkyl and R' is a divalent radical such as

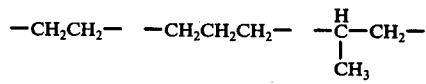

Examples of suitable polyamines include:
Ethylenediamine
Diethylenetriamine
Triethylenetetramine
Tetraethylenepentamine
Propylenediamine
Dipropylenetriamine
Tripropylenetetramine
Butylenediamine
Aminoethylpropylenediamine
Aminoethylbutylenediamine

Other polyamines in which the nitrogen atoms are separated by a carbon atom chain having 4 or more carbon atoms include the following: Tetramethylenediamine, pentamethylenediamine, hexamethylenediamine, etc.

If desired, one can prepare a variety of reactants having two or more amino groups and at least one hydroxyl group. One may use modifications of procedures or the procedures themselves as described in U.S. Pat. Nos. 2,046,720, dated July 7, 1936, to Bottoms; 2,048,990 dated July 28, 1936, to Britton et al.; 2,447,821 dated August 24, 1949, to Sankus; and 1,985,885 dated Jan. 1, 1935, to Bottoms. Examples include the following:

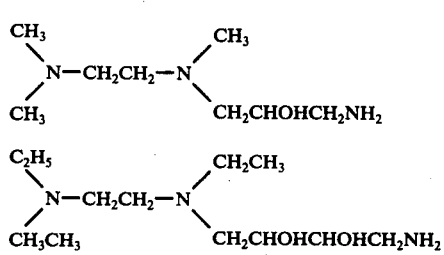

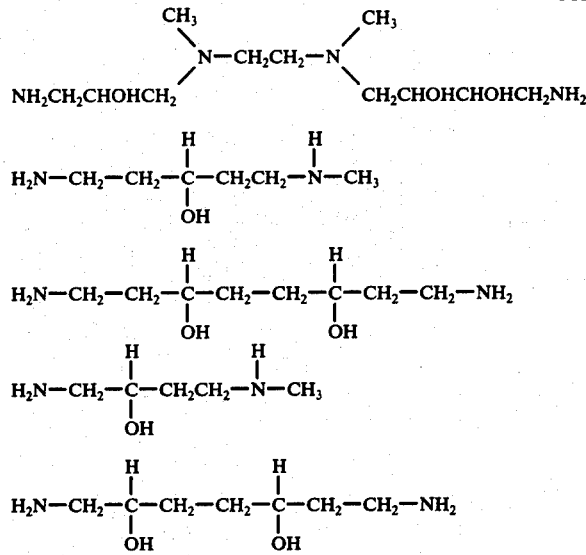

Other suitable amines are exemplified by ethylenebisoxypropylamine,

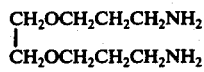

and derivatives obtained by treating ethylenebisoxypropylamine with 1, 2, 3, or 4 moles of ethylene oxide, propylene oxide, butylene oxide, or the like.

Other compounds including those having cyclic structures include piperazine, and the corresponding derivatives, etc.

Another example of polyamines which may be employed as a reactant is the kind described as "Duomeens."

Duomeen is a trademark designation for certain diamines. Duomeen have the following general formula:

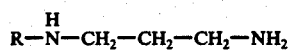

R is an alkyl group derived from a fatty acid or from the mixed fatty acids as obtained from certain oils. The specific Duomeen and the source of the radical R are as follows:

Duomeen 12-17=lauric
Duomeen C—R=Coconut oil fatty acid

Similarly, a comparable diamine, presumably obtained from Rosin Amine D and acrylonitrile, can be prepared. The structure of Rosin Amine D is as follows:

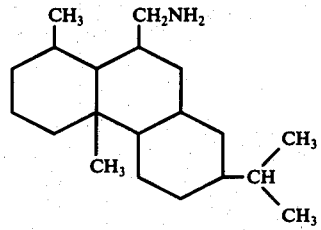

Polyamines from monoamines and cyclic imines, such as ethylene imine.

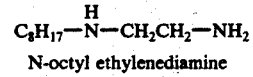
N-octyl ethylenediamine

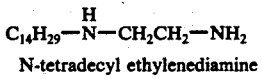
N-tetradecyl ethylenediamine

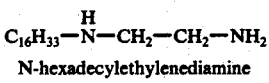
N-hexadecylethylenediamine

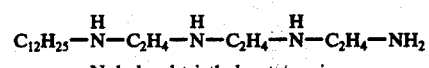
N-dodecyl triethylenetetramine

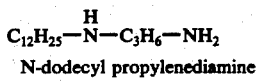
N-dodecyl propylenediamine

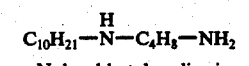
N-decyl butylenediamine

It is to be noted that all the above examples show high molal groups, i.e., 8 carbon atoms or more. The same derivatives in which methyl, ethyl, propyl, butyl, amyl, hexyl groups, or the like, appear instead of octyl, decyl, etc., are equally satisfactory.

Cyclic amidines, such as imidazolines and tetrahydropyrimidines, having an amino side chain can be reacted, for example

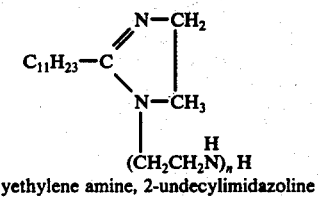
1-polyethylene amine, 2-undecylimidazoline

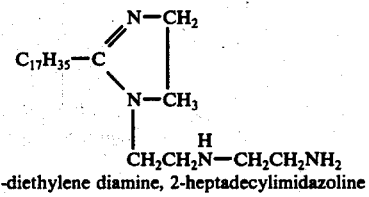
1-diethylene diamine, 2-heptadecylimidazoline

-continued

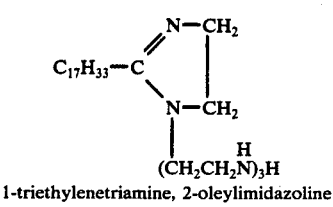
1-triethylenetriamine, 2-oleylimidazoline

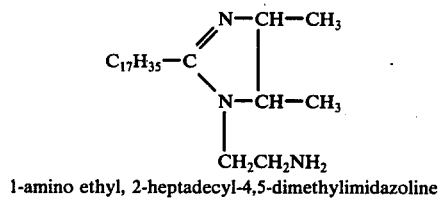
1-amino ethyl, 2-heptadecyl-4,5-dimethylimidazoline

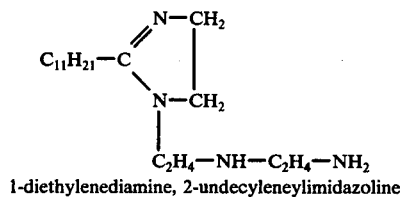
1-diethylenediamine, 2-undecyleneylimidazoline

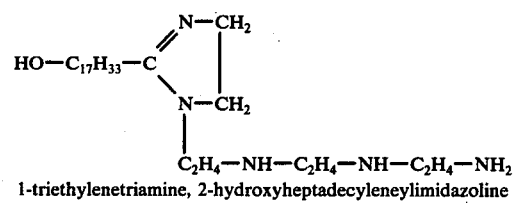
1-triethylenetriamine, 2-hydroxyheptadecyleneylimidazoline

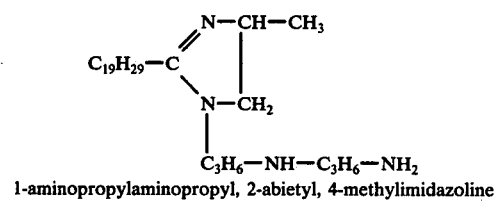
1-aminopropylaminopropyl, 2-abietyl, 4-methylimidazoline

Tetrahydropyrimidines from monocarboxy acids and trimethylenepolyamines.

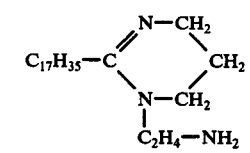
1-aminoethyl, 2-heptadecyltetrahydropyrimidine

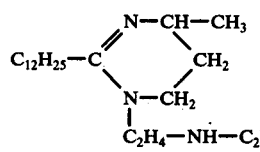
1-aminoethylaminoethyl, 2-dodecyl, 4-methyl tetrahydropyrimidine

Cyclic amidines are derived conveniently from carboxy acids, including polycarboxy acids. As is well known, some polycarboxy acids have 3 or more carboxyl radicals; thus, it is possible to obtain cyclic amidines in which 3 or more ring radicals appear.

Cyclic amidines having more than one ring are illustrated by the following formulas:

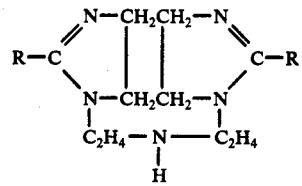

R=hydrocarbon radical containing 8–32 carbon atoms.

Cyclic amidines containing basic tertiary amino groups:

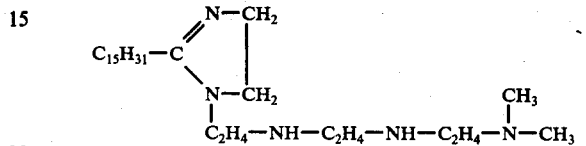

It is to be noted that all the above examples show high molal groups, i.e., 8 carbon atoms or more. The same derivatives in which methyl, ethyl, propyl, butyl, amyl, hexyl groups, or the like, appear instead of groups having 11, 12, 17 or 19 carbon atoms, are equally satisfactory.

Amino amides are also suitable as reactants for the present purpose. Such amino amides are shown as follows:

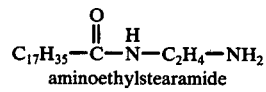
aminoethylstearamide

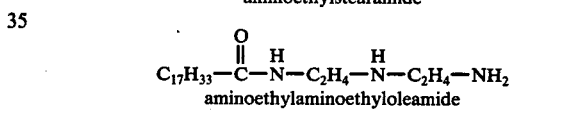
aminoethylaminoethyloleamide

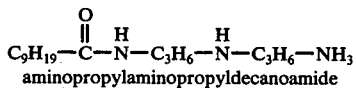
aminopropylaminopropyldecanoamide

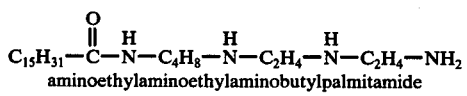
aminoethylaminoethylaminobutylpalmitamide

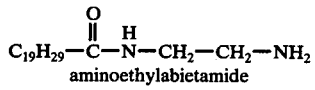
aminoethylabietamide

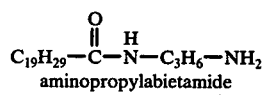
aminopropylabietamide

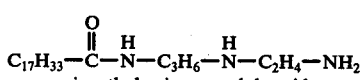
aminoethylaminopropyloleamide

Diamides may be obtained from polyamines and two moles of acid.

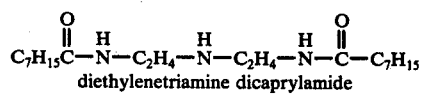
diethylenetriamine dicaprylamide

Polyamides are derived from polycarboxy acids as well as monocarboxy acids. Thus it is possible to get polyamides by using acids containing more than one carboxyl group, as illustrated in the following examples:

R—(COOH)$_2$=Emery dimeric acid available commercially and said to be dilinoleic acid.

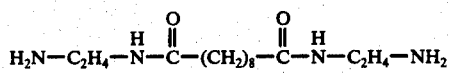

Amino amides can be obtained from polyamides in which there is a terminal tertiary amine radical having a basic nitrogen atom. Another procedure involves the production of an amino amide from a polyamine in which the terminal radicals are either primary or secondary followed by alkylation of the amide so as to convert the residual terminal radical into a basic tertiary amine radical. Another procedure is to use a secondary amine, such as dibutylamine or dihexylamine, and react stepwise with ethylene imine or propylene imine. The polyamine so obtained contains a basic tertiary amino radical. The acylation of such a polyamine results in an amino amide which will form complexes comparable to those obtained from a basic tertiary amine. Examples of such amino amides are as follows:

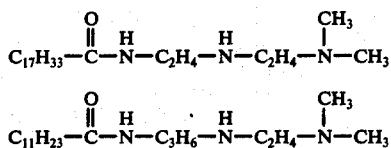

It is to be noted that all the above examples show high molal groups, i.e., 7 carbon atoms or more. The same derivatives in which methyl, ethyl, propyl, amyl, butyl, hexyl groups, or the like, appear instead of groups having 9, 17, 19 carbon atoms or the like, are equally satisfactory.

Other amines include those of the acrylonitrile and acetonecyanohydrin-polyamine reaction products such as described in the following patent applications: Ser. No. 502,636, filed Oct. 22, 1965, now U.S. Pat. No. 3,531,496, issued Sept. 29, 1970; Ser. No. 502,447, filed Oct. 22, 1965, now U.S. Pat. No. 3,450,646, issued June 17, 1969; Ser. No. 520,883, filed Jan. 17, 1966, now U.S. Pat. No. 3,488,294, issued Jan. 6, 1970.

Other amines include hydrazine and derivatives thereof, high molecular weight polyethyleneimines, polypropyleneimines, etc. having molecular weight for example above 1,000, such as 5,000 to over a million, etc., and other amidifiable amines.

These phosphoramides may be prepared by any suitable means.

The preferred reaction for the preparation of the phosphoric monoamides involves the reaction of an alkyl phosphite with a polyhalide and a secondary or primary amine. The polyhalide and dialkyl phosphite react together under basic catalysis to produce a reactive intermediate which is readily attacked by the amine to produce the phosphoric monoamide. Although carbon tetrachloride is the preferred halide in the reaction, other polyhalides such as pentachloro ethane, hexachloroethane, carbon tetrabromide, bromoform, iodoform, bromotrichloromethane and other can be used.

The following Examples are presented for purposes of illustration and not of limitation:

EXAMPLE 1

To diethyl phosphite (27.6 g: 0.2 mole) dissolved in carbon tetrachloride (150 ml.) was carefully added diethylene triamine (20 g: 0.2 mole) dissolved in carbon tetrachloride (50 ml) over a period of five minutes during which time the temperature rose from room temperature to above 50° C. After stirring for about six hours at ambient temperature, the product was extracted with water which was evaporated to yield

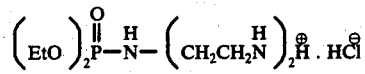

The general reaction can be presented as follows:

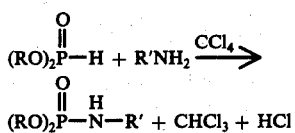

Although the procedure of Example 1 is a very convenient one, alternative procedures can be used with advantage in some cases. The use of a solvent in place of an excess of carbon tetrachloride is a particularly useful modification and is illustrated in Example 2. Further alternative procedures giving rise to phosphoramides from phosphites are described in Examples 3 and 4. Other preparations of phosphoramides, particularly using halides of phosphorus are described by Kosolapoff in "Organophosphorus Compounds" Wiley, 1950, pp 278–298.

EXAMPLE 2

To a solution of diethyl phosphite (27.6g: 0.2 mole) and carbon tetrachloride (38.5g: 0.25 mole) in ethyl alcohol (100 ml) was added diethylene triamine (20.6g: 0.2 mole) in ethyl alcohol (50 ml). The reaction temperature was maintained at 50° – 60° by controlling the rate of addition of the amine. After stirring for two hours, evaporation of the solvents gave the expected phosphoramide identical with that of Example 1.

The following Example illustrates the use of a tertiary amine to remove hydrogen chloride in the reaction of a primary amine with diethyl phosphite and carbon tetrachloride.

EXAMPLE 3

To a stirred solution of triethylamine (20.2g: 0.2 mole) and diethyl phosphite (27.6g: 0.2 mole) in carbon tetrachloride (150 ml), dodecyl amine (37.0g: 0.2 mole) in carbon tetrachloride (50 ml) was added in 15 minutes to give an exothermic reaction. After stirring at ambient temperature for three hours the triethylamine hydrochloride was removed by washing with water. Evaporation of the organic extract yielded 63.5 g: (91%) of the phosphoramide.

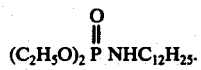

The following example illustrates the reaction of an amino imidazoline.

EXAMPLE 4

To a solution of diethyl phosphite (0.1 mole) in carbon tetrachloride (60 ml) was added 1-β-aminoethyl, 2-octadecyl 2-imidazoline (0.1 mole) in 40 ml of carbon tetrachloride during 30 minutes. An exothermic reaction took place yielding the phosphoramide 90%.

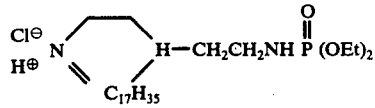

Since HCl is given off in the reaction, in the case of monoamines, it is customary to employ two moles of the amine in order to consume the HCl. In the case of polyamines, only one mole is employed since the product, being basic, will absorb HCl.

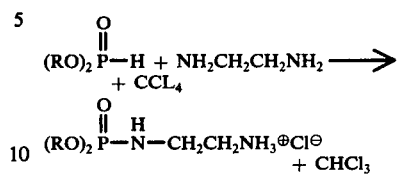

Since the following examples are similarly prepared, to save repetitive details they will be presented in the following table.

TABLE I

| Ex. | Phosphite | Mol | Amine | Mol | Formula Product | Comments |
|---|---|---|---|---|---|---|
| 5 | $(C_{12}H_{25}O)_2 \overset{O}{\underset{\|}{P}} H$ | 1 | $NH_3$ | 4 | $(C_{12}H_{25}O)_2 \overset{O}{\underset{\|}{P}} NH_2$ | |
| 6 | $(C_4H_9O)_2 \overset{O}{\underset{\|}{P}} H$ | 1 | $NH_3$ | 4 | $(C_4H_9O)_2 \overset{O}{\underset{\|}{P}} NH_2$ | |
| 7 | $(C_2H_5O)_2 \overset{O}{\underset{\|}{P}} H$ | 1 | $NH_2(CH_2)_2NH_2$ | 1 | $(C_2H_5O)_2 \overset{O}{\underset{\|}{P}} NH-$ $-(CH_2)_2 \overset{\oplus}{N}H_3$ $Cl^{\ominus}$ | |
| 8 | $(C_2H_5O)_2 \overset{O}{\underset{\|}{P}} H$ | 1 | $NH(CH_2)_3NH_2$ | 1 | $(C_2H_5O)_2 \overset{O}{\underset{\|}{P}} NH-$ $-(CH_2)_3 \overset{\oplus}{N}H_3$ $Cl^{\ominus}$ | |
| 9 | $(C_2H_5O)_2 \overset{O}{\underset{\|}{P}} H$ | 2 | $NH_2CH_2CH_2NH_2$ | 1 | $(C_2H_5O)_2 \overset{O}{\underset{\|}{P}} NH-$ $-(CH)_2 NH \overset{O}{\underset{\|}{P}} -$ $(OC_2H_5)_2$ | Et$_3$N 2 mole used to remove HCl as in Ex. 3 |
| 10 | $(C_2H_5O)_2 \overset{O}{\underset{\|}{P}} H$ | 1 | O⌒NH (morpholine) | 2 | $(C_2H_5O)_2 \overset{O}{\underset{\|}{P}} N$⌒O | |
| 11 | $(C_4H_9O)_2 \overset{O}{\underset{\|}{P}} H$ | 1 | O⌒NH (morpholine) | 2 | $(C_4H_9O)_2 \overset{O}{\underset{\|}{P}} N$⌒O | |
| 12 | $(C_{12}H_{25}O)_2 \overset{O}{\underset{\|}{P}} H$ | 1 | $NH_2(CH_2)_2NH-$ $-(CH_2)_2NH_2$ | 1 | $(C_{12}H_{25}O)_2 \overset{O}{\underset{\|}{P}} NH-$ $-(CH_2)_2NH$ $\|$ $(CH_2)_2 \overset{\oplus}{N}H_3$ $Cl^{\ominus}$ | |
| 13 | $(C_2H_5O)_2 \overset{O}{\underset{\|}{P}} H$ | 1 | $NH_2(CH_2CH_2NH)_4H$ | 1 | $(C_2H_5O)_2 \overset{O}{\underset{\|}{P}} -NH-$ $-(CH_2CH_2NH)-_4$ $\overset{\oplus}{H}_2$ $Cl^{\ominus}$ | |
| 14 | $(C_2H_5O)_2 \overset{O}{\underset{\|}{P}} H$ | 1 | Tretamine #2 | 1 | $(C_2H_5O)_2 \overset{O}{\underset{\|}{P}} NH$ $\overset{\oplus}{N}H_3$ $Cl^{\ominus}$ | Tretamine #2 is a mixture of polyalkylene amines triamine & higher |
| 15 | $(HC{\equiv}CCH_2O)_2 \overset{O}{\underset{\|}{P}} H$ | 1 | $NH_2CH_2CH_2NH_2$ | 1 | $(HC{\equiv}CCH_2O)_2 \overset{O}{\underset{\|}{P}}-$ $-NHCH_2$ $\overset{\oplus}{C}H_2NH_3 \, Cl^{\ominus}$ | |

TABLE I -continued

| Ex. | Phosphite | Mol | Amine | Mol | Formula Product | Comments |
|---|---|---|---|---|---|---|
| 16 | (HC≡CCH$_2$O)$_2$P(=O)H | 1 | NH$_2$(CH$_2$CH$_2$NH)$_2$H | 1 | (HC≡CCH$_2$O)$_2$P(=O)—NH(CH$_2$CH$_2$NH)—$_2$H$_2^\oplus$ Cl$^\ominus$ | |
| 17 | [—(OCH$_2$CH$_2$)$_2$— —OP(=O)(H)—]$_n$ | 1 equiv | NH$_2$(CH$_2$)$_2$NH—(CH$_2$)$_2$NH$_2$ | 1 | [—(OCH$_2$CH$_2$)$_2$OP(=O)— NH (CH$_2$)$_2$ NH(CH$_2$)$_2$NH$_3^\oplus$ Cl$^\ominus$]$_n$ | low M.W. polymer n=4–10 |
| 18 | [—(OCH$_2$CH$_2$)$_2$— O—P(=O)(H)—]$_n$ | 1 equiv | Tretamine #2 | 1 | [—(OCH$_2$CH$_2$)$_2$OP(=O)— NH NH$_3^\oplus$Cl$^\ominus$]$_n$ | Starting Polymer as in Ex. 17 |
| 19 | [—(OCH$_2$CH$_2$)$_x$— —OP(=O)(H)—]$_n$ | 1 equiv | NH$_2$(CH)$_2$NH(CH$_2$)$_2$—NH$_2$ | 1 | [(OCH$_2$CH$_2$)$_x$— —OP(=O)— NH (CH$_2$)$_2$ NH(CH$_2$)$_2$NH$_3^\oplus$ Cl$^\ominus$]$_n$ | x=8–12 n=4–10 |
| 20 | as in Ex. 19 | 1 | As in Ex. 19 | 4 | As in Ex. 19 | Product contains excess amine |
| 21 | [—OCH$_2$CH$_2$OCH$_2$CH$_2$— —OP(=O)(H)—]$_n$ | 1 equiv | C$_{12}$H$_{25}$NH$_2$ | 1 | [(—OCH$_2$CH$_2$OCH$_2$— —CH$_2$—O—P(=O)— NH C$_{12}$H$_{25}$]$_n$ | Et$_3$N used to remove HCl n=4–10 |
| 22 | (C$_2$H$_5$O)$_2$P(=O)H | 1 | Gilsonite Amine HNBCD 1 equiv secondary | nitrogen | (C$_2$H$_5$O)$_2$P(=O)N⌒ | Gilsonite HNBCD contains secondary & tertiary heterocyclic N |
| 23 | [—OCH$_2$CH$_2$OCH$_2$— —CH$_2$OP(=O)(H)—]$_n$ | 1 equiv | Gilsonite HNBCD 1 equiv secondary | nitrogen | [—O—CH$_2$CH$_2$OCH$_2$— —CH$_2$OP(=O)(N⌒)—]$_n$ | |

TABLE I -continued

| Ex. | Phosphite | Mol | Amine | Mol | Formula Product | Comments |
|---|---|---|---|---|---|---|
| 24 | (C$_2$H$_5$O)$_2$P(=O)H | 1 | imidazoline with NCH$_2$—, C$_{11}$H$_{23}$, —CH$_2$NH$_2$ | 1 | imidazolinium with ⊕N—CH$_2$—Cl⊖, H, C$_{11}$H$_{23}$, —CH$_2$NH P(=O)(OC$_2$H$_5$)$_2$ | Prepared as Ex. 2 using ethanol as solvent |
| 25 | (C$_2$H$_5$O)$_2$P(=O)H | 1 | imidazoline with NCH$_2$—, C$_{17}$H$_{35}$, —CH$_2$NH$_2$ | 1 | imidazolinium with ⊕N—CH$_2$—Cl⊖, H, C$_{17}$H$_{35}$, —CH$_2$NH P(=O)(OC$_2$H$_5$)$_2$ | Prepared as Ex. 2 using ethanol as solvent |
| 26 | (C$_{12}$H$_{25}$O)$_2$P(=O)H | 1 | imidazoline with N—CH$_2$—, C$_{11}$H$_{23}$, —CH$_2$NH$_2$ | 1 | imidazolinium with ⊕N—CH$_2$CH$_2$—, H Cl⊖, C$_{11}$H$_{23}$, —NH P(=O)(OC$_{12}$H$_{25}$)$_2$ | |
| 27 | (HC≡CCH$_2$O)$_2$P(=O)H | 1 | morpholine (O NH) | 2 | (HC≡CCH$_2$O)$_2$P(=O)—N(morpholine) | |

The preferred embodiment of this invention is a phosphoramide prepared from a polyamine or a polymeric phosphoramide, which polymer is prepared from either a mono-but preferably from a polyamine. The preferred polymeric structure contains an oxyalkyl phosphorus backbone with pendent amino groups, for example, of the formula

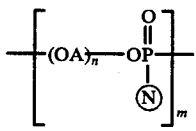

where $n$ is a number, for example of about 1 to 50 or greater, for example, about 1 - 25, such as about 1 -15, but preferably about 1 to 8. Ⓝ is derived from an amidoforming amine and $m$ is a number for example, about 2 - 40 or greater, for example about 2 to 25, such as about 2 to 15, but preferably about 2 to 10.

As is quite evident, other amines and phosphorous derivatives can be employed herein or will be constantly developed which could be useful in this invention. It is, therefore, not only impossible to attempt a comprehensive catalogue of such compositions, but to attempt to describe the invention in its broader aspects in terms of specific chemical names of reactants would be too voluminous and unnecessary since one skilled in the art could by following the description of the invention herein select proper reagents. This invention lies in the use of suitable amines and phosphorous derivatives which can be used to form phosphoramides. To precisely define each specific useful mine and phosphorous derivative in light of the present disclosure would merely call for chemical knowledge within the skill of the art in a manner analogous to a mechanical engineer who prescribes in the construction of a machine the proper materials and the proper dimensions thereof. From the description in this specification and with the knowledge of a chemist, one will know or deduce with confidence the applicability of specific amines and phosphorous derivatives suitable in this invention by applying them in the process set forth herein to form phosphoramides. In analogy to the case of a machine, wherein the use of certain materials of construction or dimensions of parts would lead to no practical useful result, various materials will be rejected as inapplicable where others would be operative. One can obviously assume that no one will wish to use a useless amine or a useless phosphorous derivative nor will be misled because it is possible to misapply the teachings of the present disclosure to do so. Thus, any amine or phosphorous derivative that can react to form phosphoramides can be employed.

USE AS CORROSION INHIBITORS

This phase of this invention relates to the use of these compounds in inhibiting the corrosion of metals, most particularly iron, steel and ferrous alloys. These compounds can be used in a wide variety of applications and systems where iron, steel and ferrous alloys are affected by corrosion. They may be employed for inhibiting corrosion in processes which require a protective or passivating coating as by dissolution in the medium which comes in contact with the metal. They can be used in preventing atmospheric corrosion, underwater corrosion, corrosion in steam and hot water systems, corrosion in chemical industries, underground corrosion, etc.

The corrosion inhibitors contemplated herein find special utility in the prevention of corrosion of pipe or equipment which is in contact with a corrosive oil-containing medium, as, for example, in oil wells producing corrosive oil or oil-brine mixtures, in refineries, and the like. These inhibitors may, however, be used in other systems or applications. They appear to possess properties which impart to metals resistance to attack by a variety of corrosive agents, such as brines, weak inorganic acids, organic acids, $CO_2$, $H_2S$, air or oxygen, etc.

The method of carrying out this process is relatively simple in principle. The corrosion preventive reagent is dissolved in the liquid corrosive medium in small amounts and is thus kept in contact with the metal surface to be protected. Alternatively, the corrosion inhibitor may be applied first to the metal surface, either as is, or as a solution in some carrier liquid or paste. Continuous application, as in the corrosive solution, is the preferred method, however.

The present process finds particular utility in the protection of metal equipment of oil and gas wells, especially those containing or producing an acidic constituent such as $H_2S$, $CO_2$, air or oxygen, organic acids and the like. For the protection of such wells, the reagent, either undiluted or dissolved in a suitable solvent, is fed down the annulus of the well between the casing and producing tubing where it becomes commingled with the fluid in the well and is pumped or flowed from the well with these fluids, thus contacting the inner wall of the casing, the outer and inner wall of tubing, and the inner surface of all wellhead fittings, connections and flow lines handling the corrosive fluid.

Where the inhibitor composition is a liquid, it is conventionally fed into the well annulus by means of a motor driven chemical injector pump, or it may be dumped periodically (e.g., once every day or two) into the annulus by means of a so-called "boll weevil" device or similar arrangement. Where the inhibitor is a solid, it may be dropped into the well as a solid lump or stock, it may be blown in as a powder with gas, or it may be washed in with a small stream of the well fluids or other liquid. Where there is gas pressure on the casing, it is necessary, of course, to employ any of these treating methods through a pressure equalizing chamber equipped to allow introduction of reagent into the chamber, equalization of pressure between chamber and casing, and travel of reagent from chamber to well casing.

Occasionally, oil and gas wells are completed in such a manner that there is no opening between the annulus and the bottom of the tubing or pump. This results, for example, when the tubing is surrounded at some point by a packing held by the casing or earth formation below the casing. In such wells the reagent may be introduced into the tubing through a pressure equalizing vessel, after stopping the flow or fluids. After being so treated, the well should be left closed in for a period of time sufficient to permit the reagent to drop to the bottom of the well.

For injection into the well annulus, the corrosion inhibitor is usually employed as a solution in a suitable solvent. The selection of solvent will depend much upon the specific reagent being used and its solubility characteristics.

For treating wells with packed-off tubing, the use of solid "sticks" or plugs of inhibitor is especially convenient. These may be prepared by blending the inhibitor with a mineral wax, asphalt or resin in a proportion sufficient to give a moderately hard and high-melting solid which can be handled and fed into the well conveniently.

The protective action of the herein described reagents appears to be maintained for an appreciable time after treatment ceases, but eventually is lost unless another application is made.

For example, for the protection of gas wells and gas-condensate wells, the amount of corrosion inhibitor used might range between about ¼ to 3 lbs. per million cubic feet of gas produced, depending upon the amounts and composition of corrosive agents in the gas and the amount of liquid hydrocarbon and water produced. However, in no case does the amount of inhibitor required appear to be stoichiometrically related to the amount of acids produced by a well, since protection is obtained with much less corrosion inhibitor than usually would be required for neutralization of the acids produced.

These compounds are particularly effective in the prevention of corrosion in systems containing a corrosive aqueous medium, and most particularly in systems containing brines.

These reagents can also be used in the prevention of corrosion in the secondary recovery of petroleum by water flooding and in the disposal of waste water and brine from oil and gas wells. Still more particularly, they can be used in a process of preventing corrosion in water flooding and in the disposal of waste water and brine from oil and gas wells is characterized by injecting into an underground formation an aqueous solution containing minor amounts of the compositions of this invention, in sufficient amounts to prevent the corrosion of metals employed in such operation.

When an oil well ceases to flow by the natural pressure in the formation and/or substantial quantities of oil can no longer be obtained by the usual pumping methods, various processes are sometimes used for the treatment of the oil-bearing formation in order to increase the flow of oil. These processes are usually described as secondary recovery processes. One such process which is used quite frequently is the water flooding process wherein water is pumped under pressure into what is called an "injection well" and oil, along with quantities of water, that have been displaced from the formation, are pumped out of an adjacent well usually referred to as a "producing well". The oil which is pumped from the producing well is then separated from the water that has been pumped from the producing well and the water is pumped to a storage reservoir from which it can again be pumped into the injection well. Supplementary water from other sources may also be used in conjunction with the produced water. When the storage reservoir is open to the atmosphere and the oil is subject to aeration this type of water flooding system is referred to herein as an "open water flooding system". If the water is recirculated in a closed system without substantial aeration, the secondary recovery method is referred to herein as a "closed water flooding system".

Because of the corrosive nature of oil field brines, to economically produce oil by water flooding, it is necessary to prevent or reduce corrosion since corrosion increase the cost thereof by making it necessary to repair and replace such equipment at frequent intervals.

I have discovered a method of preventing corrosion in systems containing a corrosive aqueous media, and most particularly in systems containing brines, which is characterized by employing the compounds described herein. For example, I have discovered an improved process of protecting from corrosion metallic equipment employed in secondary oil recovery by water flooding such as injection wells, transmission lines, filters, meters, storage links, and other metallic implements employed therein and particularly those containing iron, steel, and ferrous alloys, such process being characterized by employing in water flood operation an aqueous solution of the compositions of this invention.

The invention, then, is particularly concerned with preventing corrosion in a water flooding process characterized by the flooding medium, containing an aqueous or an oil field brine solution of these reagents.

In many oil fields large volumes of water are produced and must be disposed of where water flooding operations are not in use or where water flooding operations cannot handle the amount of produced water. Most States have laws restricting pollution of streams and land with produced waters, and oil producers must then find some method of disposing of the waste produced salt water. In many instances therefore, the salt water is disposed of by injecting the water into permeable low pressure strata below the fresh water level. The formation into which the water is injected is not the oil producing formation and this type of disposal is defined as salt water disposal or waste water disposal. The problems of corrosion of equipment are analogous to those encountered in the secondary recovery operation by water flooding.

The compounds of this invention can also be used in such water disposal wells thus providing a simple and economical method of solving the corrosion problems encountered in disposing of unwanted water.

Water flood and waste disposal operations are too well known to require further elaboration. In essence, the flooding operation is effected in the conventional manner except that the flooding medium contains a minor amount of these compounds, sufficient to prevent corrosion.

While the flooding medium employed in accordance with the present invention contains water or oil field brine and the compounds of this invention, the medium may also contain other materials. For example, the flooding medium may also contain other agents such as surface active agents or detergents which aid in wetting throughout the system and also promote the desorption of residual oil from the formation, sequestering agents which prevent the deposition of calcium and/or magnesium compounds in the interstices of the formation, bactericides which prevent the formation from becoming plugged through bacterial growth, tracers, etc. Similarly, they may be employed in conjunction with any of the operating techniques commonly employed in water flooding and water disposal processes, for example five spot flooding, peripheral flooding, etc. and in conjunction with other secondary recovery methods.

The concentration of the corrosion inhibitors of this invention will vary widely depending on the particular compound, the particular system, etc. Concentrations of at least about ¼ ppm, such as about ¾ to 7,500 ppm for example about 1 to 5,000 ppm, advantageously about 10 to 1,000 ppm, but preferably about 15 – 250 ppm may be employed. Larger amounts can also be employed such as 1.5 – 5.0% although there is generally no commercial advantage in so doing.

For example, since the success of a water flooding operation manifestly depends upon its total cost being less than the value of the additional oil recovered from the oil reservoir, it is quite important to use as little as possible of these compounds consistent with optimum corrosion inhibition. Since these compounds are themselves inexpensive and are used in low concentrations, they enhance the success of a flood operation by lowering the cost thereof.

By varying the constituents of the composition, the compounds of this invention can be made more oil or more water soluble, depending on whether the composition is to be employed in oil or water systems.

Although the manner of practicing the present invention is clear from the foregoing description, the following non-limiting specific examples are included for purposes of illustration.

EXAMPLES

These tests were run under conditions so set up as to simulate those found in an actual producing well. The test procedure involved the measurement of the corrosive action of fluids inhibited by the compositions herein described upon sandblasted SAE 1020 steel coupons measuring ¼ inch in diameter and being 4 inches long when compared to test coupons containing no inhibitor and commercial inhibitors.

Clean pint bottles were half-filled (almost 200 ml.) with seawater (i.e. tap water containing 3% by weight of the salts, magnesium chloride, calcium chloride, sodium sulfate and sodium chloride) which had been saturated with hydrogen sulfide. Those requiring inhibitor were charged with the same by pipetting calculated amounts contained in suitable solvents (water, isopropyl alcohol, mineral spirits) to give the required parts per million of inhibitor. Uninhibited blanks were run in conjunction with inhibited solutions. The bottles were now filled (total volume now about 400 ml.) leaving a small air space to allow for expansion. The weighed coupons attached to sealing caps were screwed onto the bottles and they were placed on a rotating wheel for seven days at 115° F. The coupons were then removed, cleaned electrolytically in 5% sulfuric acid (using the coupons as a cathode) and washed successively with dilute sodium hydroxide, twice with water, once with acetone and finally dried.

When the inhibitor was oil-soluble as contrasted to water-soluble, a two-phase system was used instead of the "all-brine system" and this simply consisted of using hydrogen sulfide saturated mineral spirits to replace 25% by volume of the brine.

The changes in the weights of the coupons during the corrosion test were taken as a measurement of the effectiveness of the inhibitor compositions. Protective percentage was calculated for each test coupon taken from the inhibited fluids in accordance with the following formula:

$$\frac{W_1 - W_2}{W_1} \times 100 = \text{percent protection}$$

in which $W_1$ is the loss in weight of the coupon taken from uninhibited fluids and $W_2$ is the loss in weight of coupons which were subjected to inhibited fluids.

The results obtained are presented in the following Table II.

All of the compositions prepared in Examples 1 – 27 are excellent corrosion inhibitors when tested and compared with the commercial corrosion inhibitors previously selected as the best commercial inhibitors for the corrosion system. The following examples are presented as exemplary.

TABLE II

H₂S SYSTEM
Percent Protection at Various ppm

| Inhibitor of | 4 | 8 | 16 | 32 |
|---|---|---|---|---|
| Example 1 | 82 | 81 | 82 | 90 |
| Example 9 | 32 | 99 | 85 | 80 |
| Example 11 | 84 | 86 | 85 | 80 |
| Example 14 | 86 | 75 | 47 | 58 |
| Example 16 | 41 | 53 | 95 | 91 |
| Example 17 | 80 | 67 | 98 | — |
| Example 18 | 97 | 94 | 47 | 75 |
| Example 20 | 48 | 72 | 52 | 51 |
| Commercial Inhibitor | 27 | 48 | 70 | 66 |

It is well known that most corrosion inhibitors of the film-forming or non-reducing type are not too effective in preventing corrosion in aerobic systems, i.e., containing air and/or oxygen. However, the compounds of this invention are particularly suitable for preventing corrosion in aerobic systems. For example, they are particularly suitable for systems containing oxygen such as found in "open" secondary recovery systems, cooling towers, and the like.

In this test one follows the procedure employing coupons of the type used for the H₂S test, fitted into the cap of a bottle having a high capacity of 1000 ml. The bottles are filled with 800 ml of liquid and rocked during the test period. Instantaneous corrosion rates are measured using the corrosion meter described in Ser. No. 332,399 filed Dec. 23, 1963, now U.S. Pat. No. 3,406,101, issued Oct. 15, 1968.

TEST 1
Air Saturated Seawater, 115° F.

| Compound | Concentration | Corrosion Rate |
|---|---|---|
| Example 1 | 100 ppm | 16.8 m.p.y. (mils/year) |
| Example 27 | 100 ppm | 10.2 m.p.y. |
| Uninhibited | — | 29.4 m.p.y. |

TEST 2
10% Brine — Air Saturated — 115° F.

| Example 17 | 10 ppm | 18.0 m.p.y. |
|---|---|---|
| Example 17 | 1000 ppm | 11.2 m.p.y. |
| Uninhibited | — | 22.6 m.p.y. |

These phosphoramides can also be employed in conjunction with other corrosion inhibitors, for example of the film-forming type. Non-limiting examples include the acylated polyamines such as described in U.S. Pat. Nos. Re. 23,227, 2,466,517, 2,468,163, 2,598,213 and 2,640,029. These acylated polyamines may be described as amides, imidazolines, tetrahydropyrimidines, etc.

WATER CLARIFICATION

The present invention also relates to a method for the clarification of water containing suspended matter.

Accordingly clarification of water containing suspended particles of matter is effected by adding to such water compounds of this invention.

Water containing suspended particles which may be treated by the present invention may have its origin either in natural or artificial sources, including industrial and sanitary sources. Waters containing suspended particles of natural origin are usually surface waters, wherein the particles are suspended soil particles (silt), although sub-surface waters may also be treated according to the present invention. Water having its origin in industrial process (including sanitary water) operations may contain many different varieties of suspended particles. These particles are generally the result of the particular industrial or sanitary operation concerned. Prior to discharging such industrial waste waters into natural water courses it generally is desired that the suspended matter be removed.

The present process may likewise be applied to water contained in stock or fish ponds, lakes or other natural or artificial bodies of water containing suspended solids. It may be applied to industrial water supplied either in preparation therefor, during or after use and prior to disposal. It may be applied to sanitary water supplies either for the elimination of suspended solids prior to use for such purposes, or it may be applied to such waters which have become contaminated with impurities from any source.

Most naturally occurring waters contain an amount of simple electrolytes (sodium, potassium, ammonium, calcium, aluminum salts, etc.) in excess of that necessary for the initial aggregation of the ultimate silt particles. This is likewise true of particles of suspended material in industrial or sanitary waters. The ultimate particles of silt or other materials are therefore naturally somewhat aggregated by reason of the presence of such electrolytes. However, the forces binding such ultimate particles together are not great and moreover are not such as to generally effect either rapid settling rates of the flocculated material or strong enough to prevent deflocculation.

The compounds of this invention cause rapid flocculation and also reinforce the formed aggregates of particles causing a general tightening or bonding together of the initial particles and an increased rate of coagulation and settling, thus forming a less turbid supernatant liquid.

The addition of the compounds of this invention to the water suspension should be made in such a fashion that the resulting flocculation and aggregation of the particles takes place uniformly throughout the body of water. In order to obtain a uniform addition for the compositions of the invention to the water-borne suspension it is generally desirable to prepare a relatively dilute stock solution of the compositions and then to add such solution to the body of water in the proportions indicated. Clarification may take place either in the natural body of waters or it may be caused to take place in hydraulic thickeners of known design.

The amount of the compositions to be employed will vary depending upon the amount and the degree of subdivision of the solids to be agglomerated or flocculated, the chemical nature of such solid and the particular inventive compositions employed. In general, I employ at least a sufficient amount of the compositions to promote flocculation. In general, I employ 0.005 – 10,000 ppm or more such as about 0.5 – 1,000 ppm, for example about 1 – 500 ppm, but preferably about 2 – 5 ppm. Since the economics of these processes are important, no more than the minimum amount required for efficient removal is generally employed. It is desired, of course, to employ sufficient compositions so flocculation will take place without causing the formation of stable dispersions.

The precipitating action of the compositions can be employed in the application of loading or filling materials to textiles or paper.

In the processing of fine mineral particles in aqueous suspension the flocculating agents will be especially useful. In the processing of ores to separate valuable mineral constituents from undesirable matrix constituents, it is frequent practice to grind the ore into a finely-divided state to facilitate separation steps such as selective flotation and the like. In many ore dressing procedures, the finely-divided ore is suspended in water to form a pulp or slime. After processing, it is usually desirable to dewater the pulps or slimes either by sedimentation or filtering. In such operations, certain ores are particularly troublesome in that the finely-divided ore, when suspended in water, forms a stable slime which settles very slowly, if at all. Such slimes are unsuitable for concentration of dewatering by sedimentation and are difficult to dewater by filtration because of the tendency to clog the pores of the filter, thus leading to excessively timeconsuming and inefficient operation of the filters. In some cases, for example, in certain phosphate mining operations, the formation of very stable suspensions of finely-divided mineral results not only in the loss of considerable valuable mineral as waste but also requires large expenditures for the maintenance of holding ponds for the waste. Similar problems are involved in processing gold, copper, nickel, lead, zinc, iron, such as taconite ores, uranium and other ores, and the inventive flocculating agents will be useful in these operations.

Some specific additional applications for the compositions of this invention, not intended to be limiting but merely illustrative are listed below. The compositions can be used for the clarification of beers or wines during manufacture. Another use is in processing effluents in pharmaceutical operations for the recovery of valuable products or removal of undesirable by-products. A particularly important use for these flocculating agents as in the clarification of both beet sugar and cane sugar juices in their processing. Still another use is for flocculation and recovery of pigments from aqueous suspensions thereof. The compositions will be particularly useful in sewage treatment operations as a flocculating agent. A further use is to promote by flocculation the removal of coal from aqueous suspensions thereof. In other words, the flocculating agents of the invention are generally useful for processing aqueous effluents of all types to facilitate the removal of suspended solids.

A water soluble or water dispersible compound, to the extent of effective concentration, is employed.

These compositions can also be employed in the process of flocculating white water and/or recycling of the precipitate solids in the paper making process described in U.S. Application Ser. No. 347,023, filed Feb. 24, 1964, now abandoned, and other processes described therein.

Although the manner of practicing the present invention is clear from the foregoing description, the following non-limiting specific examples are included for purposes of illustration.

Naturally occurring water from many sources, and in some instances, brine and brackish waters are used in the recovery of petroleum by secondary water-flooding operations. Clarification of the water is necessary in many instances prior to water flooding because the suspended impurities tend to plug the underground formations into which waters are pomped.

EXAMPLES

A suspension of FeS in brine was subjected to the action of the water-soluble compounds prepared herein.

In these tests, the FeS concentration is 25 parts per million and 1% and 5% brine solution were used. Metered quantities (500ml.) of the homogeneous suspension were placed into 1000 ml. beakers and stirred at 100 rpm. The compound to be tested was injected into the suspension to give final active concentrations varying between 2 through 4 parts per million. A commercial flocculant was run simultaneously at equivalent concentrations for comparison and the stirring was achieved by use of a Phipp and Bird "floc" multi-stirrer. After one minute the stirring rate was reduced to 20 to 30 rpm and maintained thus for ten minutes. At this time the stirring was stopped. The evaluation of the compound started at the moment flocculation and continued with respect to the "floc" size and rate of precipitation. The final evaluation was achieved by visual examination of the color of the resultant aqueous phase.

The results obtained by employing the water-soluble compounds of Table I, i.e., Examples 1, 2, 4, 7 through 11, 13 through 20, 22 through 24, 26 and 27, are found to be superior to the commercial flocculating agent usually employed.

These compounds are also effective in flocculating the other systems described herein.

The following is a partial list of industrial systems in which the compounds of the present invention can be employed as flocculating agents.
1. Petroleum industry
2. Food industry such as in the dairy industry, the canning, freezing and dehydration industries
3. Metal plating industry
4. Chemical and pharmaceutical industries
5. Mining industry, for example, in the phosphate mining industry such as in phosphate slimes
6. Fermentation industries, such as in alcohol, beer, yeast, antibiotics, etc. production
7. Tanning industry
8. Meat packing and slaughter house industry
9. Textile industry
10. Sugar refining industry
11. Coal industry
12. Soap industry
13. Sewage purification
14. Corn starch industry
15. Fat processing and soap industry
16. Paper industry
17. Hydroelectric plants, atomic energy operations, boiler plants, etc.

OTHER DERIVATIVES

These products may be further reacted to form derivatives thereof, for example, they may be oxyalkylated with alkylene oxides such as ethylene oxide, propylene oxide, butylene oxide, octylene oxide, alone or in combination; with styrene oxide, glycide, methyl glycide, allyl glycidyl ether, glycidyl isopropyl ether, glycidyl phenylether, diepoxides, polyepoxides, etc.

They may be reacted with alkylene imines such as ethyleneimine, propylene imine, etc., dialkylamino-epoxypropane of the structure

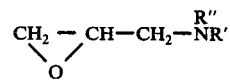

where the R's are alkyl, etc.

They may be acylated with monocarboxylic acids, such as aromatic acids, fatty acids, aliphatic acids, etc. and polycarboxylic acids aliphatic dicarboxylic acids, aromatic dicarboxylic acids for example diglycolic, phthalic, succinic, etc., acids.

These compounds may also be treated with more than one agent, for example, they may be partially acylated, then oxyalkylated, partially oxyalkylated then acylated, etc.

They may be alkylated, quaternized, used to prepare salts of organic acids, etc.

OTHER USES

In addition to the uses described above, these compositions and/or derivatives thereof, can be used as follows:

1. as demulsifiers for water-in-oil and oil-in-water emulsions
2. as biocides i.e. bacteriocides, algicides, etc.
3. as additives to various petroleum fuels including gasoline, diesel fuel, jet fuels, etc.
4. as gasoline anti-icers and anti-stallers
5. as flotation agents, such as flotation collection agents
6. as emulsifiers, for example, in metal cleaners, auto polishes, wax emulsions, etc.
7. As additives for sludging oil and cutting oils
8. as fuel "dehazing" agents
9. as agents for preparing emulsions for the "hydrofrac" process of enhancing oil recovery
10. as agents to prepare polymer emulsions
11. as agents for the textile industry such as mercerizing assistants, wetting agents, rewetting agents, penetrating agents, dispersing agents, softening agents, dyeing assistants, etc.
12. as anti-static agents for textiles, plastics, etc.
13. as agents in leather processing
14. as lube oil additives
15. as emulsifiers for insecticidal and agricultural compositions
16. as additives for rubber latices, for example, to prevent acid coagulation
17. as additives in the production of latex foam rubber, for example, as gel sensitizers and processing aids in the manufacture of foam rubber
18. as additives for primer paints to help insure adhesion to metallic surfaces and give corrosion protection
19. as additives useful as a freeze-thaw stabilizer for latex-base paints
20. as agents for the pulp and paper industry, such as sizing aids, etc.
21. as general metal deactivators
22. scale inhibitors

I claim:

1. A polymeric phosphoramide compound selected from the group consisting of polymeric phosphoramides and hydrohalide salts thereof prepared by reacting
   1. a polymeric ester of the formula

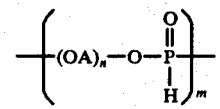

where A is an alkylene radical,
n is about 1 to 50 and
m is about 2 to 40 and
   2. ammonia, an aliphatic or cycloaliphatic or arylamine having at least one primary or secondary amino group or a mixture of said amines, in the presence of an aliphatic polyhalide reactant and a tertiary amine to form the polymeric phosphoramides and in the presence of an aliphatic polyhalide reactant alone to form the hydrohalide salts thereof.

2. The polymeric phosphoramide compound of claim 1 where (2) is an aliphatic polyamine having at least one primary or secondary amino group.

3. The hydrohalide salt of the polymeric phosphoramide of claim 2 where (1) is of the formula

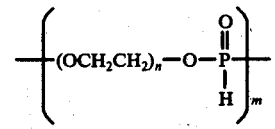

and n is 8 to 12 and m is 4 to 10
and (2) is $NH_2(CH_2)_2NH(CH_2)_2NH_2$ and said hydrohalide salt of the polymeric phosphoramide is of the formula

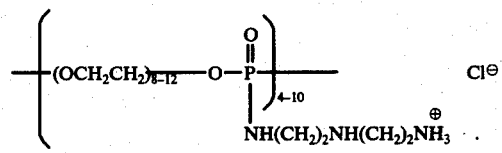

4. The hydrohalide salt of the polymeric phosphoramide of claim 2 where (1) is of the formula

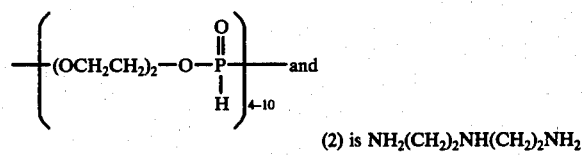

(2) is $NH_2(CH_2)_2NH(CH_2)_2NH_2$ and said hydrohalide salt of the polymeric phosphoramide is of the formula

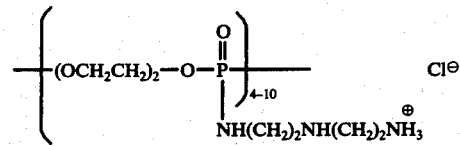

5. The polymeric phosphoramide of claim 1 where (2) is an aliphatic monoamine having at least one primary or secondary amino group.

6. The polymeric phosphoramide of claim 5 where (1) is of the formula

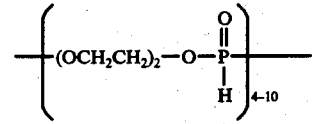

and (2) is $C_{12}H_{25}NH_2$ and said polymeric phosphoramide is of the formula

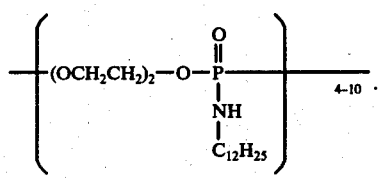

* * * * *